United States Patent [19]

Yourno

[11] Patent Number: 5,556,773
[45] Date of Patent: Sep. 17, 1996

[54] METHOD AND APPARATUS FOR NESTED POLYMERASE CHAIN REACTION (PCR) WITH SINGLE CLOSED REACTION TUBES

[76] Inventor: Joseph Yourno, 1662 New Scotland Rd., Slingerlands, N.Y. 12159

[21] Appl. No.: 292,524

[22] Filed: Aug. 18, 1994

Related U.S. Application Data

[63] Continuation-in-part of Ser. No. 103,194, Aug. 6, 1993, abandoned.

[51] Int. Cl.$^6$ .............................. C12P 19/34; C12Q 1/68; C12Q 1/70; C12N 11/02
[52] U.S. Cl. .................. 435/91.2; 435/6; 435/5; 435/177; 536/24.3; 536/0.31; 536/0.32; 536/0.33
[58] Field of Search .................. 435/6, 5, 91.2; 536/24.3–0.33

[56] References Cited

U.S. PATENT DOCUMENTS

| | | | |
|---|---|---|---|
| 4,683,195 | 7/1987 | Mullis et al. | 435/6 |
| 5,304,487 | 4/1994 | Wilding et al. | 435/291 |
| 5,314,809 | 5/1994 | Erlich et al. | 435/91.2 |
| 5,340,728 | 8/1994 | Grosz et al. | 435/91.2 |
| 5,364,591 | 11/1994 | Green et al. | 422/58 |
| 5,382,511 | 1/1995 | Stapleton et al. | 435/6 |
| 5,413,924 | 5/1995 | Kosak et al. | 435/177 |

OTHER PUBLICATIONS

Yourno, "A Method for Nested PCR with Single Closed Reaction Tubes", PCR Methods and Applications, Aug. 15, 1992, pp. 61–65.
Mullis et al., "Specific Synthesis of DNA in Vitro Via a Polymerase–Catalyzed Chain Reaction", Methods in Enzymology, Academic Press, vol. 155, 1987, pp. 335–350.

Primary Examiner—W. Gary Jones
Assistant Examiner—Dianne Rees
Attorney, Agent, or Firm—Schmeiser, Olsen & Watts

[57] ABSTRACT

A nested polymerase chain reaction (PCR) performed in a single reaction tube that remains closed after the reaction mixtures for each amplification have been introduced therein. The reaction mixture for the second PCR amplification is sequestered and preserved in an upper portion of the single, closed reaction tube during the first amplification, and subsequently introduced into the reaction space containing the end product of the first PCR amplification, without opening the reaction tube.

8 Claims, 1 Drawing Sheet

METHOD AND APPARATUS FOR NESTED POLYMERASE CHAIN REACTION (PCR) WITH SINGLE CLOSED REACTION TUBES

This is a Continuation-in-Part of my U.S. patent application Ser. No. 08/103,194, filed on Aug. 6, 1993, entitled METHOD AND APPARATUS FOR NESTED POLYMERASE CHAIN REACTION (PCR) WITH SINGLE CLOSED REACTION TUBES, now abandoned.

FIELD OF THE INVENTION

The present invention relates to the detection of target nucleic sequences and, more particularly, to a method and apparatus for performing a double (nested) polymerase chain reaction (PCR) in a single reaction tube which remains closed during both amplifications.

BACKGROUND OF THE INVENTION

Conventional PCR is unequivocally sufficient for the detection of "single-copy" sequences of nucleic acid, such as those represented in the genomic or chromosomal DNA of human cells, since the source material is usually derived from hundreds to thousands of cells. Unfortunately, when conventional PCR is employed in the detection of rare target sequences such as from viruses and other low-level infectious agents, or a few cancer cells among a large population of normal cells, the target sequences oftentimes remain undetectable or indeterminate (negative or borderline amplification signal). As such, nested PCR procedures have been developed to increase the amplifying power of conventional PCR manyfold, thereby greatly enhancing the sensitivity of detection of rare target nucleic acid sequences such as from the HIV provirus, cancer cells, or the like.

As is well known in the art, conventional nested PCR procedures utilize two sequential amplification processes. Specifically, the two sequential amplification processes include a first amplification process comprising at least one amplification step for amplifying an extended target sequence, and a second, subsequent amplification process comprising at least one amplification step for amplifying an internal sequence from the product of the first amplification process, wherein the internal sequence may or may not overlap one of the ends of the extended sequence. Each amplification step of the first amplification process employs an outer primer set typically comprising a pair of outer primers. Similarly, each amplification step of the second amplification process employs an inner primer set typically comprising a pair of inner primers. The above-described techniques of conventional nested PCR have been well known for almost a decade as evidenced by the Mullis et al. article "Specific Synthesis of DNA in Vitro via a Polymerase-Catalyzed Chain Reaction", in METHODS IN ENZYMOLOGY, Academic Press, Vol. 155, 1987, pp. 335–350, incorporated herein by reference. The two sequential amplification processes of the nested PCR procedure detailed above are utilized in the present invention.

The enhanced sensitivity of nested PCR is achieved by carefully controlling the reaction conditions for the first and second amplification processes to favor the generation of the desired product. In addition to the usual considerations, most nested PCR procedures require a severalfold excess of inner over outer primers in the second amplification process for satisfactory results. Conventional nested PCR procedures generally accomplish this by amplifying only a small aliquot of the completed first amplification mixture after transfer to a new reaction tube for the second amplification process. Unfortunately, the greatly enhanced sensitivity provided by conventional nested PCR procedures is bought at the price of potential false positives, because the reaction tubes containing high concentrations of the first amplification product must be opened and manipulated to set up the second amplification, thereby increasing the probability of contamination.

SUMMARY OF THE INVENTION

In order to avoid the disadvantages of the prior art, the present invention provides a method and apparatus for nested PCR using a single reaction tube that remains closed during the first and second amplification processes after the reaction mixtures for both amplifications processes have been introduced therein. More specifically, the reaction mixture for the second PCR amplification process is sequestered and preserved in an upper portion of the single, closed reaction tube during the first amplification process, and then introduced into the reaction space containing the end product of the first amplification process. Advantageously, the closed-tube nested PCR of the present invention combines the sensitivity of conventional nested PCR with the specificity of conventional unnested PCR. It is particularly suited to supplement both conventional types of PCR where increased analytical power is desirable to detect and analyze low-level target sequences of nucleic acid, including primary detection in specimens and quantitation of DNA (including complementary DNA produced from RNA) by limiting dilution of specimens, and it forms the basis of a reliable, automated methodology for nested PCR.

The reaction tube of the present invention includes a ungasketed or gasketed screw-top having a central chamber for separating the reaction mixture for the second PCR amplification process from the reaction mixture for the first PCR amplification process. The reaction mixture for the first PCR amplification process is set up in a conventional manner in the reaction tube and overlaid with a shield of mineral oil. Preferably, the outer primer pair of the first PCR amplification process is provided at a reduced concentration which is sufficient to produce plateau amplification. The reaction mixture for the second PCR amplification process, prepared to provide a severalfold excess of inner over outer primers in the second amplification process to assure a nested PCR procedure having a high specificity and sensitivity, is prepared in a melted, thin agarose gel matrix which is subsequently introduced into the central chamber of the reaction tube screw-top where it remains sequestered in a semisolid state during the first PCR amplification process. After the first PCR amplification process has been completed, the reaction mixture for the second PCR amplification process is introduced into the reaction space through centrifugation, mixed in by reheating, and the second PCR amplification process is performed as usual.

Many other techniques may be utilized to separate the reaction mixture for the second PCR amplification process from the reaction mixture for the first PCR amplification process within the single, closed reaction tube. For example, a thin, frangible membrane formed of molded plastic or other suitable materials may be utilized to sequester the reaction mixture for the second PCR amplification process, prepared in liquid form, within an upper portion of the reaction tube, wherein the frangible membrane is robust enough to support and contain the reaction mixture for the second PCR amplification process but thin enough to rupture when subjected to centrifugation or other sufficient forces.

Other modifications of the present invention are based upon the containment of the reaction mixture for the second PCR amplification process over a snap-cap floor under the screw-cap or in the top of a long, thin rod and tube (similar to a hematocrit tube) inside the reaction tube. Alternately, a "medicine-dropper" like bulb, attached to the top of the reaction tube, may be used to contain a reaction mixture for the second PCR amplification process. As should be readily apparent, a plethora of additional configurations may be utilized to segregate the reaction mixtures for the first and second PCR amplification processes within the reaction tube without departing from the scope of the present invention.

The closed tube process of the present invention may be used for multiple, sequential amplifications and associated processes (e.g. messenger RNA [mRNA] reverse transcription into complementary DNA [cDNA]). For example, an original target sequence consisting of RNA may be reverse transcribed into cDNA by the enzyme reverse transcriptase in a one step reverse transcription process, then the cDNA amplified in one or more sequential amplification processes of PCR, wherein the reverse transcription and amplification processes are performed in a single closed reaction container. Thus, the RNA may be detected, or quantitated by limiting dilution of the final DNA amplification product or by other techniques. It would merely be necessary to sequester the reaction mixtures for successive amplification processes in serially disposed chambers of the closed container and to release the reaction mixtures serially for successive amplifications or associated processes. This is easily accomplished by differential centrifugation (using a series of thin frangible membranes having varying strengths) or by sequentially pumping serially placed reaction mixtures into the reaction space each segmented in a length of tubing and seperated by a barrier as single as an airlock or a mineral oil segment.

BRIEF DESCRIPTION OF THE DRAWINGS

These and other features of the present invention will become readily apparent upon reading the following detailed description and upon reference to the drawings in which.

DETAILED DESCRIPTION OF THE INVENTION

Figure 1:
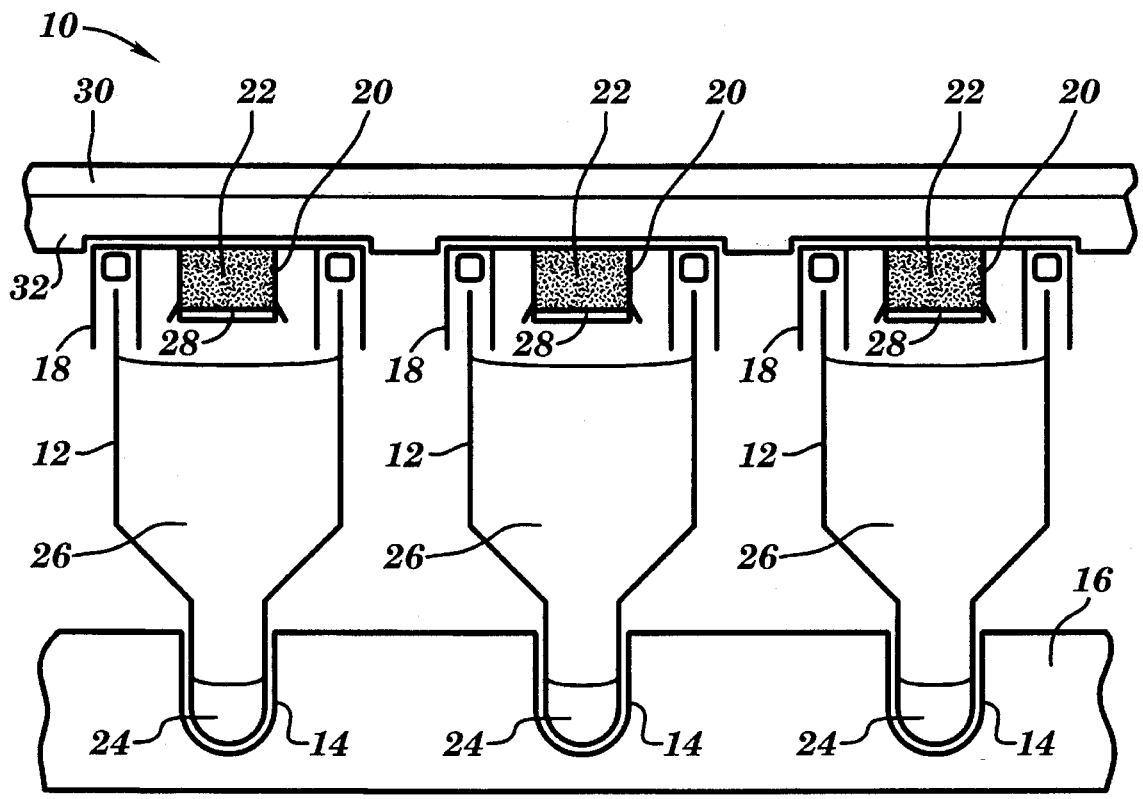
FIG. 1 illustrates a closed-tube nested PCR configuration in accordance with the present invention.

Referring now specifically to the drawings, there is illustrated an apparatus for performing a nested polymerase chain reaction with single closed reaction tubes in accordance with the present invention, wherein like reference numerals refer to like elements throughout the drawings.

As illustrated in FIG. 1, the closed-tube nested PCR configuration, generally designated as 10, includes a plurality of reaction tubes 12, such as the ungasketed 0.5-ml Gene Amp reaction tubes manufactured by Perkin-Elmer Cetus or the gasketed 1.0-ml reaction tubes manufactured by Sarstedt, which are supported within the wells 14 of a thermal cycler block 16. Each of the reaction tubes 12 includes a screw-cap 18 incorporating a centrally disposed central chamber 20 on the interior, underside thereof for receiving and sequestering a hanging gel matrix 22 containing the reaction mixture for the second PCR amplification process therein.

The reaction mixture 24 the first PCR amplification process is set up in a conventional manner and aliquoted into the bottom of each reaction tube 12. Prior to the initiation of the first PCR amplification process, an aliquot of a purified agarose stock gel in a PCR buffer is remelted by heating and combined with the components of the second PCR amplification so as to produce a melted, thin agarose gel matrix containing the reaction mixture for the second PCR amplification process. After inverting each screw-cap 18, the liquified, thin agarose gel matrix containing the second PCR amplification reaction mixture is aliquoted into the upwardly directed chambers 20 thereof, allowed to solidify into the gel matrix 22 and overlaid with a desiccation-inhibiting layer of mineral oil 28. As illustrated in FIG. 1, the screw-caps 18 containing the gel matrix 22 are subsequently secured onto the reaction tubes 12 after the tube dead space above the first PCR amplification reaction mixture 24 has been filled with a mineral oil shield 26, thereby forming the closed reaction tubes of the present invention. Preferably, each reaction tube 12 is filled with mineral oil to just below the screw-cap 18, thereby creating a small insulating airspace below the adherent hanging gel matrix 22.

In a first embodiment of the present invention, the thin agarose gel matrix containing the reaction mixture for the second PCR amplification is prepared from stock aliquots of 0.375% agarose in 1.5×PCR buffer which are stored at −20° C. For each closed-tube nested PCR procedure, an aliquot of the buffer/gel is melted by boiling, and the other components of the second PCR amplification process are added at room temperature directly to the melted gel/buffer. After mixing and a brief rewarming, and prior to the sealing of each reaction tube 12, the melted, thin agarose gel matrix containing the reaction mixture for the second PCR amplification process is aliquoted into chambers 20 as described above.

As is well known in the art, the thermal cycler block 16 is adapted to subject the lower end of the reaction tubes 12 to a plurality of high temperature thermal cycles during both the first and second PCR amplification processes of a nested PCR procedure, wherein each high temperature thermal cycle corresponds to an amplification step. In the present invention, a cooling plate 30 and associated deformable conductive blanket 32 are provided to cool and protect the hanging gel matrix 22 from the extreme temperature changes to which the lower end of the tubes 12 are subjected during the first PCR amplification process.

Figure 2:
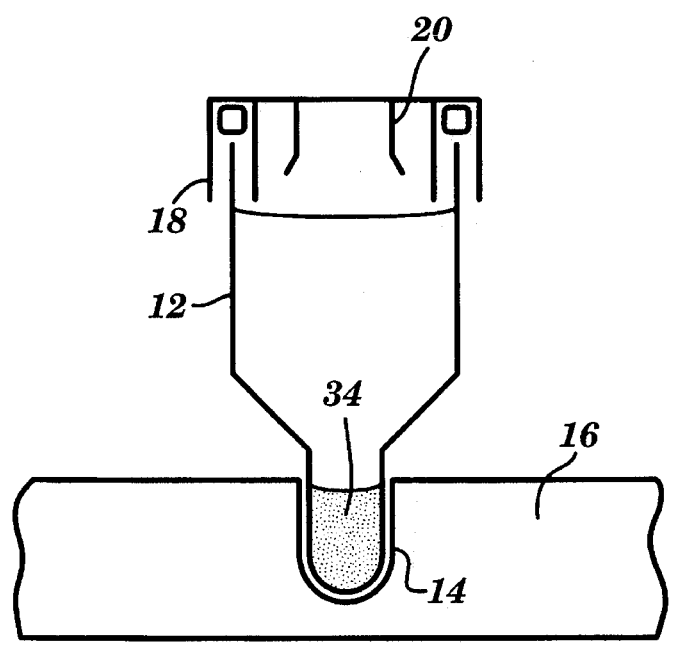
FIG. 2 illustrates one of the closed reaction tubes of FIG. 1, after the reaction mixture for the second PCR amplification process has been introduced into the reaction space containing the end product of the first PCR amplification process.

As illustrated in FIG. 1, the hanging gel matrix 22 is sequestered within the chamber 20 during the first PCR amplification process. After the completion of the first PCR amplification process and the removal of the cooling plate 30 and conductive blanket 32, the reaction mixture for the second PCR amplification process is introduced into the reaction space containing the end product of the first PCR amplification process, and the second PCR amplification process is performed as usual. More specifically, as illustrated in FIG. 2, the hanging gel plug 22 is dislodged from the screw cap underside and is introduced into the reaction space by centrifugation, melted by brief heating to about 100° C. and mixed into the end product of the first PCR amplification process in response to the reheating and centrifugation of the tube 12, thereby forming a reaction mixture 34 containing the end product of the first PCR amplification process and the reaction mixture for the second PCR amplification process. After the second amplification is performed, aliquots of the reaction mixture are removed from the reaction container and analysed by conventional techniques such as gel electrophoresis and florescence or hybridization with labelled probed for the target nucleic acid sequences.

The foregoing description of the preferred embodiments of the invention has been presented for purposes of illustration and description. It is not intended to be exhaustive or to limit the invention to the precise form disclosed, and obviously many modifications and variations are possible in light of the above teaching. Such modifications and variations that may be apparent to a person skilled in the art are intended to be included within the scope of this invention as defined by the accompanying claims.

I claim:

1. A method for performing a nested polymerase chain reaction in a single, closed reaction container, wherein said nested polymerase chain reaction includes first and second amplification processes each comprising at least one amplification step, each amplification step of said first amplification process employing an outer primer set including at least one outer primer, each amplification step of said second amplification process employing an inner primer set including at least one inner primer, comprising the steps of:

introducing a reaction mixture containing the outer primer set for the first amplification process of said nested polymerase chain reaction into a first portion of said reaction container;

physically sequestering a reaction mixture containing the inner primer set for the second amplification process of said nested polymerase chain reaction in a second portion of said reaction container;

closing said reaction container, said reaction container remaining closed during the first and second amplification processes of said nested polymerase chain reaction;

performing the first amplification process of said nested polymerase chain reaction using the reaction mixture for said first amplification process;

introducing the reaction mixture for the second amplification process of said nested polymerase chain reaction into the first portion of said reaction container after performing said first amplification process; and performing the second amplification process of said nested polymerase chain reaction.

2. The method for performing a nested polymerase chain reaction in a single, closed reaction container according to claim 1, wherein the reaction mixture for the first amplification process of said nested polymerase chain reaction is introduced into a lower portion of said reaction container, and wherein the reaction mixture for the second amplification process of said nested polymerase chain reaction is sequestered in an upper portion of said reaction container.

3. The method for performing a nested polymerase chain reaction in a single, closed reaction container according to claim 1, further including the step of:

mixing an end product of the first amplification process of said nested polymerase chain reaction with the reaction mixture for the second amplification process of said nested polymerase chain reaction, said mixing step occurring prior to the step of performing said second amplification process, but after said introducing the reaction mixture for the second amplification process of said nested polymerase chain reaction into the first portion of said reaction container after performing said first amplification process, allowing the reaction mixture for the second amplification process to contact the reaction mixture for the first amplification process.

4. A method for performing a nested polymerase chain reaction in a single, closed reaction container, wherein said nested polymerase chain reaction includes first and second amplification processes each comprising at least one amplification step, the at least one amplification step of said first amplification process employing an outer primer set including at least one outer primer, the at least one amplification step of said second amplification process employing an inner primer set including at least one inner primer, comprising the steps of:

introducing a reaction mixture containing the outer primer set for the first amplification process of said nested polymerase chain reaction into said reaction container;

introducing a reaction mixture containing the inner primer set for the second amplification process of said nested polymerase chain reaction into a physically sequestered portion of said reaction container, closing said reaction container;

performing the first amplification process of said nested polymerase chain reaction using the reaction mixture for the first amplification process; and performing the second amplification process of said nested polymerase chain reaction after combining an end product of the first amplification process with the reaction mixture for the second amplification process, wherein the first and second amplification processes of said nested polymerase chain reaction are sequentially performed without opening said reaction container.

5. The method of claim 2, wherein the reaction mixture including the inner primer set for the second amplification process is sequestered from the reaction mixture including the outer primer set for the first amplification process by being contained in an agarose gel which is suspended in a central chamber of the upper portion.

6. The method of claim 5, wherein the reaction mixture including the inner primer set for the second amplification process is sealed within the central chamber by a frangible membrane, and wherein the introducing step is performed by centrifuging the reaction container, so that the frangible membrane ruptures, allowing the reaction mixture including the inner primer set for the second amplification process to drop into the lower portion of the reaction container.

7. The method of claim 6, further comprising a mixing step performed by heating the reaction container until the reaction mixture including the inner primer set for performing the second amplification process melts and mixes with the product of the first amplification process in the lower portion of the reaction container.

8. The method of claim 1, wherein the reaction mixture including the inner primer set for the second amplification step is sequestered by means of an inert shielding material in a piece of tubing attached to and pressure sealed from a lower portion of the reaction container and wherein the introducing step is performed by sequentially pumping the reaction mixture including the inner primer set for the second amplification step into the lower portion of the reaction container.

\* \* \* \* \*

UNITED STATES PATENT AND TRADEMARK OFFICE
CERTIFICATE OF CORRECTION

PATENT NO. : 5,556,773
DATED : September 17, 1996
INVENTOR(S) : Youmo

It is certified that error appears in the above-identified patent and that said Letters Patent is hereby corrected as shown below:

Column 6, line 40, "5" should read --2--.

line 48, "6" should read --5--.

Signed and Sealed this

Seventeenth Day of December, 1996

Attest:

BRUCE LEHMAN

*Attesting Officer*      *Commissioner of Patents and Trademarks*